(12) United States Patent
Kim et al.

(10) Patent No.: US 7,157,605 B2
(45) Date of Patent: Jan. 2, 2007

(54) METHOD FOR PREPARING 4-AMINODIPHENYLAMINE

(75) Inventors: Jin-eok Kim, Daejeon (KR); Jong-cheon Park, Seoul (KR); Kil-sun Lee, Daejeon (KR); Jung-hee Jang, Gwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 11/225,087

(22) Filed: Sep. 14, 2005

(65) Prior Publication Data
US 2006/0258887 A1    Nov. 16, 2006

(30) Foreign Application Priority Data
May 16, 2005    (KR) .................. 10-2005-0040667

(51) Int. Cl.
*C07C 209/00*    (2006.01)
(52) U.S. Cl. .................................................... 564/420
(58) Field of Classification Search ................. 564/420
See application file for complete search history.

(56) References Cited

U.S. PATENT DOCUMENTS

| 5,684,203 | A | 11/1997 | Jautelat | |
| 6,395,933 | B1 * | 5/2002 | Triplett et al. | 564/420 |
| 6,583,320 | B1 * | 6/2003 | Triplett et al. | 564/420 |

* cited by examiner

*Primary Examiner*—Samuel Barts
(74) *Attorney, Agent, or Firm*—Mayer, Brown, Rowe & Maw LLP

(57) ABSTRACT

4-aminodiphenylamine is prepared by reacting carbanilide and nitrobenzene in an adequate solvent, which may be nitrobenzene, in the presence of an appropriate organic base, which may be tetramethylammonium hydroxide, alone or in mixture with an inorganic base and subsequently reducing the reaction product in the presence of an appropriate catalyst and hydrogen gas. The subsequent reduction may be carried out on the reaction mixture before the reaction mixture is subjected to separation.

21 Claims, No Drawings

METHOD FOR PREPARING 4-AMINODIPHENYLAMINE

BACKGROUND OF THE INVENTION

1. Field of the Invention

The present invention relates to a method for preparing 4-aminodiphenylamine (hereunder referred to as "4-ADPA") from carbanilide (diphenylurea) and nitrobenzene. More particularly, it relates to a method for preparing 4-ADPA by the reaction of carbanilide and nitrobenzene, in the presence of an appropriate organic base or a mixture of an organic base and an inorganic base, to prepare 4-nitrodiphenylamine (hereunder referred to as "4-NDPA") and 4-nitrosodiphenylamine (hereunder referred to as "4-NODPA") with good selectivity and yield and continuously reducing these 4-nitro- or 4-nitroso-diphenylamine intermediates with an appropriate catalyst and hydrogen without a separation process, i.e., without separating the 4-NDPA and 4-NODPA intermediates.

2. Description of the Related Art

In general, 4-ADPA is widely used to prepare (N-(1,3-dimethylbutyl)-N'-phenyl-p-phenylenediamine) ("6PPD"), (N-isopropyl-N-phenyl-p-phenylenediamine) ("IPPD"), etc., by reductive alkylation, which may be utilized as anti-aging agents of rubbers.

The known industrial preparation processes of 4-ADPA can be classified into three groups. They are the Monsanto process, the Ouchi process and the NASH (nucleophilic aromatic substitution for hydrogen) process.

In the Monsanto process, chlorobenzene is nitrated to p-chloronitrobenzene, and then reacted with formanilide to prepare 4-NDPA. Then, 4-NDPA is hydrogenated to prepare 4-ADPA. In this preparation method, treatment of corrosive wastewater containing chlorine and a large amount of organic and inorganic waste liquids are required.

In the Ouchi process, diphenylamine is reacted with sodium nitrite ($NaNO_2$) to prepare N-nitrosodiphenylamine, which undergoes Fischer-Hepp rearrangement, neutralized and then hydrogenated to prepare 4-ADPA. This process has the problem of generation of a large volume of harmful waste liquid during the nitrosation process.

The third process, or NASH process, has been proposed as an alternative to the above processes generating harmful materials.

One NASH process involves directly reacting aniline and nitrobenzene in the presence of base, such as, tetramethylammonium hydroxide (hereunder referred to as "TMAH") to prepare 4-NDPA and 4-NODPA (*J. Am. Chem. Soc.*, 1992, 114(23), 9237–8; U.S. Pat. No. 5,117,063; U.S. Pat. No. 5,252,737; U.S. Pat. No. 5,331,099; U.S. Pat. No. 5,453,541; U.S. Pat. No. 5,552,531; U.S. Pat. No. 5,633,407). This process is able to reduce the amount of waste and environmentally harmful materials.

However, this method is disadvantageous in that excessive byproducts, such as, 2-nitrodiphenylamine (hereunder referred to as "2-NDPA"), phenazine and azobenzene, are generated because aniline tends to react at the ortho site of nitrobenzene.

Other proposed methods of preparing 4-ADPA include head-to-tail addition of aniline (U.S. Pat. No. 4,760,186) and hydrogenation of p-nitrosodiphenylhydroxylamine. However, these methods are disadvantageous in production efficiency and in economic aspect. As a new preparing method using the NASH reaction process to prepare 4-ADPA, reaction of aniline and azobenzene in the presence of base such as TMAH (*J. Org. Chem.*, 1994, 59(19), 5627–5632; U.S. Pat. Nos. 5,382,691 and 5,618,979, EP No. 726,889, WO No. 95/12569, JP No. 9504546) is also known. But, this method is also disadvantageous in production yield.

Another method of using the NASH reaction with an anilide as starting material, involves reacting acetanilide and nitrobenzene in a DMSO solvent in the presence of NaOH and $K_2CO_3$ to prepare 4-NODPA (*Tetrahedron Letters*, vol. 31, No. 22, pp 3217–3210, 1990). However, the acetanilide is unstable under the reaction conditions and by-products are generated by the decomposition of starting materials.

More recently, the NASH reaction has been used to react carbanilide and nitrobenzene in a dimethylsulfoxide (hereunder referred to as "DMSO") solvent in the presence of NaOH, an inorganic base, to prepare 4-NDPA (U.S. Pat. No. 5,684,203, WO No. 0051966). This method requires recycling of the inorganic base and use of the expensive DMSO solvent. Also, removal of DMSO solvent is required prior to hydrogenation to avoid possible poisoning of precious metal catalyst.

SUMMARY OF THE INVENTION

According to one embodiment, the present invention provides an economical method for preparing 4-ADPA by continuously hydrogenating 4-NDPA and 4-NODPA, formed by the NASH reaction of carbanilide and nitrobenzene, in the presence of a reactive organic base or a mixture of organic base and inorganic base, which does not require use of DMSO or an inorganic base for the reaction of carbanilide and nitrobenzene.

According to another embodiment of the invention a method for preparing 4-ADPA is provided whereby reaction time may be reduced and amount of by-product generated may also be reduced.

In various embodiments of the invention, there is provided a method for preparing 4-ADPA by reacting carbanilide and nitrobenzene in an organic solvent system in the presence of an organic base or a mixture of organic base with an inorganic base, and hydrogenating the resulting 4-nitrodiphenylamine (4-NDPA) and 4-nitrosodiphenylamine (4-NODPA) intermediates, without separating the 4-NDPA and 4-NODPA from each other. The processes according to the various embodiments of the invention are capable of reducing amount of wastes without adversely affecting the continuous hydrogenation.

In a particular embodiment of the invention, a recyclable organic base, such as TMAH, with good reactivity in a common organic solvent is used as the base, thereby eliminating the requirement for expensive organic solvents, such as, DMSO and hexamethylphosphoramide (hereunder referred to as "HMPA"), which are generally required, using an inorganic base, such as, alkali metal or alkaline earth metal bases.

DETAILED DESCRIPTION OF PREFERRED EMBODIMENTS

The present invention relates to a method for preparing 4-ADPA from carbanilide and nitrobenzene. More particularly, it relates to a method for preparing 4-ADPA which includes reacting carbanilide and nitrobenzene in the presence of an appropriate organic base or a mixture of an organic base and an inorganic base to prepare 4-NDPA and 4-NODPA with good selectivity and yield and continuously reducing them with an appropriate catalyst and hydrogen without requiring a separation process.

According to embodiments of the present invention, 4-NDPA and 4-NODPA can be selectively obtained in good yield.

The present invention uses carbanilide, also known as diphenylurea, which can be easily prepared from urea and aniline, as starting material.

The present invention in its various embodiments, uses a recyclable organic base to drive the reaction between carbanilide and nitrobenzene. Because recycling of the organic base may be maximized, generation of waste water can be significantly reduced.

As organic base, an organic base easy to collect and recycle after reaction may be used alone or in combination with an alkali metal inorganic base. The organic base may be, for example, tetraalkylammonium hydroxides or alkyl-substituted diammonium hydroxides. For the tetraalkylammonium hydroxides, tetramethylammonium hydroxide (TMAH) or one generating TMAH is conveniently used and provides good results. Mixtures of organic bases may also be used.

The organic base may be used alone or together with an inorganic base. Representative examples of suitable inorganic bases include alkali metal hydroxides or alkaline earth metal hydroxides, such as, for example, sodium hydroxide (NaOH), potassium hydroxide (KOH), calcium hydroxide; alkali metal hydrides or alkaline earth metal hydrides, such as, for example, sodium hydride, calcium hydride; or a mixture of any of the foregoing. A mixture of organic base and inorganic base may be referred to hereinunder as "mixture base."

In addition to the organic base alone, or the mixture base, a phase transfer catalyst may be used during the NASH reaction in accordance with embodiments of the invention. For example, mention may be made of crown ethers, tetraalkylammonium salts, such as, for example, tetraalkylammonium chloride, as phase transfer catalyst.

In embodiments of the present invention in which a mixture base is used, the mixture base may comprise from about 30 to about 90 mol % of organic base and from about 10 to about 70 mol % of inorganic base. As the content of inorganic base becomes larger, recycling of the base is difficult and reactivity decreases.

Generally, the total amount of base used may be in the range of from about 1 to about 10, such as from about 2 to about 5, molar equivalents of carbanilide. As the content of the base becomes larger, formation of by-products, such as azobenzene, azoxybenzene and phenazine, tends to increase. Conversely as the amount of base becomes smaller, reactivity tends to decrease. Those skilled in the art will, therefore, be readily able to determine the optimum amount of base material(s).

The reaction between carbanilide and nitrobenzene, in the presence of the recyclable organic base (alone or as a mixture with an inorganic base and/or phase transfer catalyst) is carried out in the presence of a solvent not affecting the NASH reaction. For example, toluene, benzene, N-methyl-2-pyrrolidinone (hereunder referred to as "NMP"), tetrahydrofuran (hereunder referred to as "THF"), dioxane, ethylene glycol dimethyl ether and nitrobenzene may be used, alone or in combination, as the solvent. One of ordinary skill in the art would be able to determine other solvents which may be used without adversely effecting the NASH reaction between carbanilide and nitrobenzene, e.g., providing good reactivity and/or good yield, and without adversely affecting the subsequent continuous reduction of the intermediate by-products 4-NDPA and 4-NODPA, to 4-ADPA, e.g., interfering with the reduction reaction yields, etc. For example, it is one of the advantages of the embodiments of the present invention that it is not necessary to use dimethylsulfoxide ("DMSO") (which is often preferred in the prior art because of its allegedly high yields) or other solvents, which, like DMSO, are expensive and/or tend to poison the precious metal catalysts which are often preferably used to effect reduction of 4-NDPA and/or 4-NODPA.

Nitrobenzene, itself, which is used as reactant, may, in accordance with a preferred embodiment of the invention, be also used, at the same time, as a or the solvent, since it affects neither the NASH reaction nor the continuous hydrogenation.

In accordance with other embodiments of the invention, toluene or benzene, either of which can effectively remove water generated during the reaction, may be used as solvent, alone or in admixture with each other and/or in admixture with nitrobenzene, and/or in admixture with such other suitable solvent as mentioned above or otherwise determined by routine experimentation to not adversely effect either of the NASH reaction or the subsequent reduction reaction.

When selecting the solvent, in addition to avoiding solvents that tend to adversely affect catalyst activation during the reduction (e.g., continuous hydrogenation) reaction step, it is generally desirable to choose a solvent system that is capable of effectively separating the organic base from the aqueous phase (e.g., formed from water produced during the NASH reaction). In this regard, mention may be made of, for example, nitrobenzene, toluene, nitrobenzene or ethylene glycol dimethyl ether. Again, as noted above, these solvents may be used alone or in admixture with each other or with other suitable solvent as described herein.

Generally, the proportion, by weight, of solvent(s) to carbanilide may be in the range of from 1–50 parts by weight solvent to 1 part by weight, preferably 3–30 parts by weight of solvent to 1 part by weight of carbanilide.

Following the NASH reaction between carbanilide and nitrobenzene, the resulting solution, including the recyclable organic base, 4-NDPA and 4-NODPA, may be directly hydrogenated with an adequate catalyst, for example, Pt/C or Pd/C, without separation. Alternatively, TMAH, or other organic base, may be removed from the aqueous phase of the reaction solution and then the remaining organic phase may be reduced, such as by hydrogenation, to obtain 4-ADPA. After hydrogenation, the solvent and aniline (produced by hydrogenation of unreacted nitrobenzene) and any other volatile components included in the reaction solution may be removed, for example, by vacuum distillation, and then other, less volatile by-products, such as, for example, azobenzene and phenazine by-products, which may be produced, may be removed, by any suitable separation process, as well known to those skilled in the art, to obtain coarse 4-ADPA residual. Finally, the coarse 4-ADPA may be purified, for example, under a high temperature, vacuum distillation condition to obtain pure or at least very high purity, 4-ADPA.

In the conventional NASH reaction of aniline and nitrobenzene, the separation of 4-NDPA and 4-NODPA becomes difficult as a result of by-products, such as, 2-NDPA and phenazine generated by ortho attack. When carbanilide is used as starting material, the steric hindrance caused by the amide structure greatly reduces by-product formation due to the ortho attack.

Accordingly, in the embodiments of the present invention, the amount of waste can be minimized because the organic base is recyclable, corrosion of the reactor can be prevented because no corrosive chlorine-containing waste water is generated and reaction time decreases and production yield of 4-NDPA and 4-NODPA increases because highly reactive carbanilide is used.

In preferred embodiments of the present invention, nitrobenzene is used in amounts within the range of from about 1 to about 30, preferably, from 2 to about 30, more preferably, from 3 to about 30, such as, for example, from 2 or 3 to about 10 or 20, molar equivalents of carbanilide. As the amount of nitrobenzene increases, the reaction rate and production yield per given time tend to increase. However, if the content of nitrobenzene becomes too large, azoxybenzene is generated as by-product, thereby reducing selectivity of 4-NDPA. Therefore, the amount of nitrobenzene is desirable kept at an amount not higher than about 30 molar equivalents, more preferably, at an amount not higher than about 10 molar equivalents, of carbanilide. Conversely, if the content of nitrobenzene becomes lower than about 1 mole per mole of carbanilide, the proportion of un-reacted carbanilide tends to increase, therefore, decreasing the yield.

Where nitrobenzene is used primarily as reactant rather than as reactant and solvent, the molar ratio of nitrobenzene to carbanilide will generally fall within the range of from about 1:1 to about 5:1.

The reaction temperature may generally be within the range of from about 0° C. to about 150° C., more preferably 50° C. to about 80° C. As the reaction temperature decreases, the reaction rate tends to decrease. At a reaction temperature above about 150° C., generation of by-products increases, so that production yield of 4-NDPA and 4-NODPA decreases.

Water is generated during the NASH reaction and, in order to improve production yield, the formed water may be removed by vacuum distillation or by using a drying agent. Anhydrous potassium carbonate, anhydrous sodium sulfate, anhydrous magnesium sulfate, sodium hydroxide, potassium hydroxide, sodium hydride or a molecular sieve may be used as the drying agent.

According to embodiments of the present invention, the reaction is performed at normal pressure under nitrogen or oxygen atmosphere, or under vacuum. Under nitrogen atmosphere, by-products, such as, azobenzene and azoxybenzene tend to be generated, but generation of azoxybenzene is minimized under oxygen or air atmosphere. However, it is not necessary to particularly limit the reaction atmosphere, because azobenzene and azoxybenzene can be easily converted into aniline by hydrogenation for recycling.

In the following examples, analysis of reactants and products was performed with a nuclear magnetic resonance (NMR) spectrometer and a gas chromatography-mass spectrometer detector (GC-MSD). Quantitative analysis was performed by high performance liquid chromatography (hereunder referred to as "HPLC") and gas chromatography (hereunder referred to as "GC").

HPLC analysis conditions for measuring carbanilide conversion ratio and yield of 4-NDPA and 4-NODPA was as follows. HPLC column: Waters 5C18-AR-II (4.6×150 mm); Solvent condition:

| | Solvent condition | | |
|---|---|---|---|
| Time (min) | Flow rate (mL/min) | Water (%) | Acetonitrile (%) |
| 0 | 1 | 65 | 35 |
| 25 | 1 | 0 | 100 |
| 30 | 1 | 65 | 35 |

GC analysis conditions for quantitative analysis of 4-ADPA prepared from the NASH reaction of carbanilide and nitrobenzene and subsequent hydrogenation was as follows:

Capillary column: ULTRA 2 (Crosslinked 5% Ph Me Silicon)

50 m×0.2 mm×0.33 μm

Carrier gas: Nitrogen

Head pressure: 18 psig

Oven: 100° C. (2 min) to 280° C., β=10° C./min

Detector (temperature): FID (280° C.)

Split ratio: 50:1

Carrier gas flow-rate: 38 mL

For the quantitative analysis of each product, pyrene was used as an internal standard substance. Also, the factors of gas chromatography on each product were applied to its area rate before analysis so as to calculate the molar ratio (mole %) of each product on the basis of initially added carbanilide.

The following examples illustrate embodiments for preparing 4-NDPA and 4-NODPA intermediates and 4-ADPA, but it will be appreciated that these are presented only for assisting the understanding of the present invention and are not to be construed as limiting the scope thereof.

EXAMPLES

Experimental Example 1

12.7 g (60 mmole) of carbanilide and 36.9 g (300 mmole) of nitrobenzene were put in a 200 mL, 3-necked round bottom flask equipped with a cooler and a stirrer. After heating the flask to 80° C., 23.9 g (132 mmole) of TMA (OH).5H$_2$O was added. Reaction was performed for 3 hours while keeping the degree of vacuum at about 90–50 mmHg and distilling water.

500 mg of pyrene was added as internal standard at the early step of the reaction (This procedure was applied to all experimental examples and examples).

Ethyl acetate was added to the reaction solution. The solution was neutralized with water and acetic acid. The ethyl acetate layer was separated and analyzed by HPLC.

The conversion ratio of carbanilide was 99%. The production yield was 90 mole % 4-NDPA and 8 mole % 4-NODPA, based on carbanilide. By-products included 8 mole % phenazine, 9 mole % azobenzene and 27 mole % azoxybenzene, based on carbanilide.

Experimental Example 2

Production yield of 4-NDPA and 4-NODPA was compared for various nitrobenzene contents.

12.7 g (60 mmole) of carbanilide and 4 to 10 molar equivalents of nitrobenzene were put in a 200 mL, 3-necked round bottom flask equipped with a cooler and a stirrer. After heating the flask to 80° C., 21.7 g (120 mmole) of TMA (OH).5H$_2$O was added. Reaction was performed for 3 hours while keeping the degree of vacuum at about 90–50 mmHg and distilling water.

Ethyl acetate was added to the reaction solution. The solution was neutralized with water and acetic acid. The ethyl acetate layer was separated and analyzed by HPLC.

The results are shown in Table 1.

TABLE 1

| Nitrobenzene content* (molar equivalents) | Products (mole %)** | | | | |
|---|---|---|---|---|---|
| | 4-NDPA | 4-NODPA | Phenazine | Azobenzene | Azoxybenzene |
| 4 | 76 | 9 | 4 | 7 | 24 |
| 5 | 84 | 8 | 4 | 7 | 25 |
| 10 | 88 | 4 | 7 | 4 | 12 |

*Molar equivalents of nitrobenzene per initial carbanilide.
**Production yield per initial carbanilide (mole %).

Experimental Example 3

Production yield of 4-NDPA and 4-NODPA was compared for various base contents.

12.7 g (60 mmole) of carbanilide and 36.9 g (300 mmole) of nitrobenzene were put in a 200 mL, 3-necked round bottom flask equipped with a cooler and a stirrer. After heating the flask to 80° C., 21.7 g (120 mmole) of TMA (OH).5H$_2$O was added. Reaction was performed for 3 hours while keeping the degree of vacuum at about 90–50 mmHg and distilling water.

Ethyl acetate was added to the reaction solution. The solution was neutralized with water and acetic acid. The ethyl acetate layer was separated and analyzed by HPLC.

The conversion ratio of carbanilide was 92%. The production yield was 84 mole % 4-NDPA and 8 mole % 4-NODPA, based on carbanilide. By-products included 4 mole % phenazine, 7 mole % azobenzene and 25 mole % azoxybenzene, based on carbanilide.

Experimental Example 4

Production yield of 4-NDPA and 4-NODPA was compared for various reaction temperatures.

6.4 g (30 mmole) of carbanilide and 36.9 g (300 mmole) of nitrobenzene were put in a 200 mL, 3-necked round bottom flask equipped with a cooler and a stirrer. At varying temperatures, as shown below in Table 2, 10.9 g (60 mmole) of TMA(OH).5H$_2$O was added. Reaction was performed for 3 hours while keeping the degree of vacuum at about 90–50 mmHg and distilling water.

Ethyl acetate was added to the reaction solution. The solution was neutralized with water and acetic acid. The ethyl acetate layer was separated and analyzed by HPLC.

The results are shown in Table 2.

TABLE 2

| Reaction temp. (° C.) | Products (mole %)* | | | | |
|---|---|---|---|---|---|
| | 4-NDPA | 4-NODPA | Phenazine | Azobenzene | Azoxybenzene |
| 100 | 37 | 4 | 3 | 10 | 17 |
| 80 | 84 | 8 | 4 | 7 | 25 |
| 70 | 79 | 4 | 3 | 7 | 21 |

*Production yield per initial carbanilide (mole %).

Experimental Example 5

Production yield of 4-NDPA and 4-NODPA was compared for various mixture bases including TMA(OH).5H$_2$O and inorganic bases.

6.4 g (30 mmole) of carbanilide and 36.9 g (300 mmole) of nitrobenzene were put in a 200 mL, 3-necked round bottom flask equipped with a cooler and a stirrer. After heating the flask to 80° C., a mixture of bases, including TMA(OH).5H$_2$O and inorganic bases, was added. Reaction was performed for 3 hours while keeping the degree of vacuum at about 90–50 mmHg and distilling water.

Ethyl acetate was added to the reaction solution. The solution was neutralized with water and acetic acid. The ethyl acetate layer was separated and analyzed by HPLC.

The results are shown in Table 3.

TABLE 3

| | Products (mole %)* | | | | |
|---|---|---|---|---|---|
| Bases | 4-NDPA | 4-NODPA | Phenazine | Azobenzene | Azoxybenzene |
| 30 mmole TMA(OH).5H$_2$O + 30 mmole NaOH | 52 | 6 | — | 10 | 8 |
| 30 mmole TMA(OH).5H$_2$O + 60 mmole NaOH | 85 | 6 | — | 9 | 17 |
| 30 mmole TMA(OH).5H$_2$O + 60 mmole KOH | 38 | 3 | — | 3 | 10 |

*Production yield per initial carbanilide (mole %).

Experimental Example 6

Production yield of 4-NDPA and 4-NODPA was compared for various solvents.

12.7 g (60 mmole) of carbanilide and 36.9 g (300 mmole) of nitrobenzene were put in a 200 mL, 3-necked round bottom flask equipped with a cooler and a stirrer. 64 mL of reaction solvent was added to the flask. After heating the flask to 80° C., 21.7 g (120 mmole) of TMA(OH).5H$_2$O was added. Reaction was performed for 3 hours while varying reaction conditions, as shown in Table 4, below.

Ethyl acetate was added to the reaction solution. The solution was neutralized with water and acetic acid. The ethyl acetate layer was separated and analyzed by HPLC.

The results are shown in Table 4.

TABLE 4

| | Reaction condition (mmHg) | Products (mole %)* | | | |
|---|---|---|---|---|---|
| Solvents | | 4-NDPA | 4-NODPA | Phenazine | Azoxy-benzene |
| Toluene | 300 | 35 | 9 | 2 | — |
| Toluene | 760 | 10 | 7 | — | — |
| THF | 760 | 9 | 3 | — | — |
| DMSO | 760 | 50 | 4 | — | 15 |
| Benzene | 760 | 24 | 10 | 2 | 5 |
| Nitrobenzene | 760 | 29 | 3 | — | — |

*Production yield per initial carbanilide (mole %).

Example 1

4-ADPA was prepared from the reaction solution including 4-NDPA and 4-NODPA by hydrogenation without a separation process.

12.7 g (60 mmole) of carbanilide and 36.9 g (300 mmole) of nitrobenzene were put in a 200 mL, 3-necked round bottom flask equipped with a cooler and a stirrer. After heating the flask to 80° C., 23.9 g (132 mmole) of TMA(OH).5H$_2$O was added. Reaction was performed for 3 hours while keeping the degree of vacuum at about 90–50 mmHg and distilling water. 100 mL toluene and 20 mL of water were added to the reaction solution. The water phase was separated and the organic phase containing the product was added to a high-pressure reactor. 0.3 g of 5% Pd/C (dry) was added to the reactor and air inside the reactor was substituted by hydrogen. Reduction reaction was performed for 1 hour while keeping the reaction temperature at 80° C. and the hydrogen pressure at 15 kg/cm$^2$. Conversion ratio of 4-NDPA and 4-NODPA was 100% and production yield of 4-ADPA was 90%.

As described above, the method of the present invention enables preparation of a 4-aminodiphenylamine with good selectivity and yield while reducing generation of such by-products as phenazine and 2-nitrodiphenylamine by directly reacting highly reactive and selective carbanilide with nitrobenzene. It also minimizes generation of wastes because it uses a recyclable organic base. The 4-aminodiphenylamine intermediate may be continuously reduced to prepare 4-aminodiphenylamine, or the target product, in good yield without a separation process. The method of the present invention significantly reduces the amount of harmful wastes, differently from the conventional preparation methods, and generates no environment-damaging corrosive materials.

What is claimed is:

1. A method for preparing 4-aminodiphenylamine comprising:
    reacting carbanilide and nitrobenzene in an adequate organic solvent system in the presence of an organic base under conditions to achieve a selectivity to 4-nitrodiphenylamine and 4-nitrosodiphenylamine of at least about 41% and
    hydrogenating the resulting products.

2. The method of claim 1, wherein the organic base is tetraalkylammonium hydroxide or alkyl-substituted diammonium hydroxide.

3. The method of claim 2, wherein the tetraalkylammonium hydroxide is used and is tetramethylammonium hydroxide.

4. The method of claim 1, wherein the solvent is at least one solvent selected from the group consisting of toluene, and benzene.

5. The method of claim 1, wherein the solvent is or comprises nitrobenzene.

6. The method of claim 1, wherein water generated during the reaction between carbanilide and nitrobenzene is removed under reduced pressure or using a drying agent.

7. The method of claim 6, wherein a drying agent is used and is at least one member selected from the group consisting of anhydrous potassium carbonate, anhydrous sodium sulfate, anhydrous magnesium sulfate, sodium hydroxide, potassium hydroxide, sodium hydride and molecular sieve.

8. The method of claim 1, wherein nitrobenzene is used in an amount within the range of from about 1 to about 30 molar equivalents per 1 mole of carbanilide.

9. The method of claim 1, wherein the weight ratio of solvent to carbanilide is within the range of from about 1:1 to about 50:1.

10. The method of claim 1, wherein the reaction of carbanilide and nitrobenzene is performed at a temperature within the range of from about 0° C. to about 150° C.

11. The method of claim 1, wherein the reaction of carbanilide and nitrobenzene is performed under nitrogen or oxygen atmosphere or under vacuum.

12. The method of claim 1, wherein the reduction is performed by contacting the reaction mixture with hydrogen in the presence of an adequate catalyst.

13. The method of claim 12, wherein the catalyst comprises a palladium on carbon or platinum on carbon hydrogenation catalyst.

14. The method of claim 12, wherein the reduction is performed on the reaction mixture before the reaction mixture is subjected to a separation process.

15. The method of claim 1, wherein the reduction is performed on the reaction mixture before the reaction mixture is subjected to a separation process.

16. A method for preparing 4-aminodiphenylamine comprising:

reacting carbanilide and nitrobenzene in an adequate organic solvent system in the presence of an organic base or a mixed base of organic base and an inorganic base, at a temperature in the range of from about 50° C. to about 80° C. and a reduced pressure, wherein selectivity to 4-nitrodiphenylamine and 4-nitrosodiphenylamine is at least about 41% and hydrogenating the resulting products.

17. The method of claim 16, wherein the inorganic base comprises sodium hydroxide, potassium hydroxide or a mixture thereof.

18. The method of claim 16, wherein the reduced pressure is in the range of from about 90 to about 50 mm Hg.

19. The method of claim 16, wherein the organic base is tetramethylammonium hydroxide.

20. The method of claim 16, wherein the inorganic base is sodium hydroxide.

21. The method of claim 16, wherein the selectivity is at least about 58%.

* * * * *